(12) United States Patent
Cheng

(10) Patent No.: US 10,806,466 B2
(45) Date of Patent: Oct. 20, 2020

(54) HIGH SPEED DRILL CONFIGURED WITH MULTIPLE CUTTING BURR ATTACHMENTS

(71) Applicant: Gyrus ACMI, Inc., Southborough, MA (US)

(72) Inventor: Ming J. Cheng, West Warwick, RI (US)

(73) Assignee: Gyrus Acmi, Inc., Southborough, MA (US)

( * ) Notice: Subject to any disclaimer, the term of this patent is extended or adjusted under 35 U.S.C. 154(b) by 211 days.

(21) Appl. No.: 15/908,018

(22) Filed: Feb. 28, 2018

(65) Prior Publication Data
US 2019/0262009 A1    Aug. 29, 2019

(51) Int. Cl.
*A61B 17/16*    (2006.01)

(52) U.S. Cl.
CPC ........ *A61B 17/1624* (2013.01); *A61B 17/162* (2013.01); *A61B 17/1617* (2013.01); *A61B 17/1622* (2013.01); *A61B 17/1631* (2013.01)

(58) Field of Classification Search
CPC ... A61B 17/16; A61B 17/1617; A61B 17/162; A61B 17/1622; A61B 17/1624; A61B 17/1637; A61B 2017/3407
USPC ........................................... 433/76, 102–135
See application file for complete search history.

(56) References Cited

U.S. PATENT DOCUMENTS

| | | | |
|---|---|---|---|
| 4,197,645 A * | 4/1980 | Scheicher | A61B 17/1673 408/42 |
| 2007/0123899 A1* | 5/2007 | Zhou | A61B 17/1675 606/88 |
| 2010/0241130 A1* | 9/2010 | Deli | A61F 9/00763 606/107 |
| 2014/0155896 A1* | 6/2014 | Cournoyer | A61B 17/1617 606/79 |
| 2015/0230821 A1 | 8/2015 | Batchelor et al. | |
| 2016/0008011 A1* | 1/2016 | Kostrzewski | A61B 17/162 606/80 |
| 2016/0081699 A1 | 3/2016 | Edwards | |
| 2017/0281286 A1* | 10/2017 | Braun | A61B 17/3403 |
| 2017/0319225 A1* | 11/2017 | Salehi | A61B 17/1671 |

* cited by examiner

*Primary Examiner* — George J Ulsh
(74) *Attorney, Agent, or Firm* — Schwegman Lundberg & Woessner, P.A.

(57) ABSTRACT

Systems and methods for a high speed drill cutting burr are described. The high speed drill may comprise a main body having a first section and a second section, the first section comprising a first housing configured to be operably connectable to a first cutting tip and the second section comprising a second housing configured to be operably connectable to a second cutting tip, and an electrical motor disposed inside the main body, the electrical motor may be configured to be in electrical communication with a power source. In some embodiments, a main body may be repositioned by rotating the main body 180° to switch between use of a first cutting tip and a second cutting tip. Mechanisms for limiting axial movement of a burr shank as well as transferring torque are described.

19 Claims, 7 Drawing Sheets

HIGH SPEED DRILL CONFIGURED WITH MULTIPLE CUTTING BURR ATTACHMENTS

FIELD OF THE DISCLOSURE

The embodiments of the present disclosure relate generally to a medical device. More particularly, the embodiments of the present disclosure relate to powered high speed hand tools such as high speed drills, burrs, saws, etc.

BACKGROUND

High speed drills may be implemented in various types of surgeries, including neurosurgery, ear nose and throat (ENT) procedures, and plastic surgery, for example. A surgeon, by holding the hand piece in their hand, can manipulate the rotating cutting implement to grind, shave, or cut desired tissue, bone, and/or other bodily material. Tissue abrading used in connection with conventional surgical procedures can cause overheating at the tip and may affect the tissue being reduced or abraded. Such heating becomes an issue or concern when the tissue may become modified as a result of the temperature rise at the cutting element rather than through the intended mechanical abrasion. Such heating can also cause heating of the surrounding tissue thereby leading to collateral tissue being damaged. For example, devices comprising rotating burrs in connection with ear, nose, and throat (ENT) surgical procedures can lead to collateral tissue damage as well as accidental tissue damage during extraction.

High speed drills used in surgical procedures can experience up to 85,000 rotations per minute (rpm). Thus, high speed drills can be subject to high torques and, consequently, overheating, and may be more likely to break down over time as a result. Conventional high speed drills which experience high torques may also likely experience rapid vibrations and/or distracting clicking sounds (i.e. chattering).

Conventional high speed drills employ two-stage power train assemblies. Some conventional high speed drills transmit power from a motor to a drive shaft in a first stage and from the drive shaft to a burr in a second stage via a gear-to-gear power train. This path may result in unnecessary energy losses and less efficient operation, in addition to overheating.

SUMMARY

It would be advantageous in view of the above discussion to provide systems and methods for a high speed drill capable of meeting the above-identified needs. More specifically, it would be advantageous to provide a more stable device with better surgical outcomes and a longer usable life.

The present disclosure provides an improved high speed drill comprising: (1) a first end for receiving a first drill attachment; (2) a second end for receiving a second drill attachment; (3) the first end and the second end are positioned opposite each other on a working end of a main body; (4) a two ball mechanism for locking axial movement of a burr shank; (5) a mechanism for transferring torque directly to a burr shank via an extension of a burr shank mechanically linked to a motor shaft; (6) a universal joint for transferring rotational motion from a drive shaft to a burr shank; (7) a clutch for engaging or disengaging operation of an electrical motor for a given end of the high speed drill.

Accordingly, pursuant to one aspect of the present invention, there is contemplated a medical device, comprising a main body having a first section and a second section, the first section comprising a first housing configured to be operably connectable to a first cutting tip, and the second section comprising a second housing configured to be operably connectable to a second cutting tip, and an electrical motor disposed inside the main body, the electrical motor configured to be in electrical communication with a power source.

The medical device may be further characterized by one or any combination of the features described herein, such as the first section and the second section are positioned 180° opposed from each other on the handpiece, the first cutting tip is a straight cutting burr and the second cutting tip is an angled cutting burr, wherein the first cutting tip and the second cutting tip are not mechanically connected to the electrical motor at a given time, the electrical motor is configured to transfer power to the first cutting tip or the second cutting tip via a one-stage power train assembly, a motor shaft is configured to transfer torque from a motor to a burr shank through an extension from the burr shank engaged with the motor shaft, a motor shaft is configured to transfer torque from a motor to a burr shank through an extension from a drive shaft engaged with the motor shaft, a pair of ball connectors resiliently contained within at least the first housing, the pair of ball connectors are positioned opposite each other radially about a shaft of the first cutting tip or the second cutting tip, the pair of ball connectors are configured to limit axial motion of the first cutting tip or the second cutting tip and configured to rotate during rotation of a burr shank, the second housing comprises a universal joint, the second housing further comprises a male cone configured to engage with a motor shaft, a clutch for limiting operation to a single cutting tip at a time, the clutch includes a clutch ring, the clutch ring is configured to engage a set of bearings adjacent a motor to permit rotational motion of the motor shaft.

Pursuant to another aspect of the present invention, there is contemplated a medical device, comprising a hand piece having a first end and a second end, the first end configured to be detachably connectable to a first cutting tip, and the second end configured to be detachably connectable to a second cutting tip, and an electrical motor disposed inside the hand piece, the electrical motor configured to be in electrical communication with a power source, wherein the first cutting tip and the second cutting tip are not both mechanically connected to the electrical motor at a given time.

The medical device may be further characterized by one or any combination of the features described herein, such as the electrical motor is configured to transfer torque via a first mechanism and a housing is configured to limit axial motion of a burr shank via a second mechanism.

Pursuant to another aspect of the present disclosure, there is contemplated a method for operating a high speed drill comprising inserting a straight cutting burr into a first section of a hand piece, grinding, shaving, or cutting of desired tissue, bone, and/or other bodily material, removing the straight cutting burr from the hand piece, repositioning the hand piece, and inserting an angled cutting burr into a second section of a hand piece.

The medical device may be further characterized by one or any combination of the features described herein, such as activating a clutch, and grinding, shaving, or cutting desired tissue, bone, and/or other bodily material using the angled cutting burr.

Pursuant to another aspect of the present disclosure, there is contemplated a method for operating a high speed drill comprising inserting an angled cutting burr into a second section of a hand piece, activating a clutch, grinding, shaving, or cutting desired tissue, bone, and/or other bodily material using the angled cutting burr, releasing the clutch, removing the angled cutting burr from the hand piece, repositioning the hand piece, inserting a straight cutting burr into a first section of the hand piece, grinding, shaving, or cutting desired tissue, bone, and/or other bodily material using the straight cutting burr.

The disclosure may be further characterized by one or any combination of the features described herein, such as repositioning the hand piece involves rotating the hand piece 180° about a main tubular member.

The claimed subject matter is not intended to be limited to a composition or method that must satisfy one or more of any stated objects or features of the devices described herein. It is also important to note that the claimed subject matter is not limited to the exemplary or primary embodiments described herein. Modifications and substitutions by one of ordinary skill in the art are considered to be within the scope of the disclosure.

Further aspects, advantages and areas of applicability will become apparent from the description provided herein. It should be understood that the description and specific examples are intended for purposes of illustration only and are not intended to limit the scope of the present disclosure.

Figure 1:
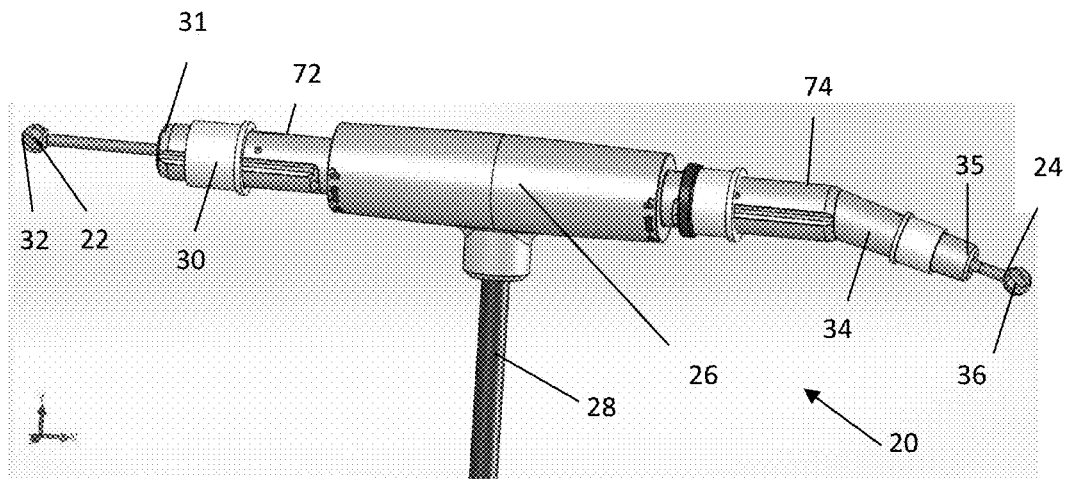
FIG. 1 illustrates a perspective view of a high speed drill, in accordance with an embodiment of the present disclosure.

These and other features of the present embodiments will be understood better by reading the following detailed description, taken together with the figures herein described.

The accompanying drawings are not intended to be drawn to scale. For purposes of clarity, not every component may be labeled in every drawing.

DETAILED DESCRIPTION

The present invention features a surgical instrument and a surgical apparatus embodying such a surgical instrument. The disclosure features a surgical instrument comprising a rotating cutting instrument. The disclosure features a surgical instrument configured for improved attachment mechanisms and features for a straight cutting burr and an angled cutting burr. The disclosure features a surgical instrument configured for distinct attachment mechanisms and features for a straight cutting burr and an angled cutting burr. The high speed drill and associated methods described herein provide an improved configuration that is configured to result in less overheating and longer service lifetimes.

A high speed drill is provided which is configured to reduce overheating. A high speed drill is provided which is configured to extend usable lifetimes. A high speed drill is provided which is configured to minimize rapid vibrations and/or chattering. A high speed drill is provided with improved power transmission efficiency. A high speed drill is provided which is configured to minimize the distance between the motor and the operable tip. A high speed drill is provided comprising a one-stage power train assembly. A high speed drill is provided comprising a reduced part count that is configured to simplify the manufacturing process and reduce costs.

The high speed drill described herein can be configured to grind, shave, or cut desired tissue, bone, and/or other bodily material. The high speed drill described herein can be configured with dual attachment ports off of a main body for connecting rotating burr tips. The high speed drill described herein can be configured for improved power transmission efficiency. In some embodiments, the high speed drill described herein is configured for direct engagement of the burr proximal end to a motor shaft. In some embodiments, the high speed drill described herein is configured with a single stage power transfer from the motor to the burr tip. The high speed drill described herein is configured with a reduced part count for simplification of the manufacturing process.

It may be desirable to provide a surgical instrument as described herein which further includes a mechanism for directly cooling the cutting element or burr to further minimize temperature rise in surrounding tissue. Thus, in some examples, high speed drill 20 is configured to be configured with certain features of the high speed drill described, for example in application Ser. No. 14/863,544, entitled HIGH-SPEED POWERED HAND TOOL WITH IMPROVED MOTOR COOLING, filed Sep. 24, 2015, which is incorporated by reference herein in its entirety. In some examples, high speed drill 20 is configured with a cooling apparatus as described, for example in application Ser. No. 14/624,070, entitled HEAT PIPE COOLED BURR INCLUDING SURGICAL INSTRUMENTS EMBODYING SAME, filed Feb. 15, 2015, which is incorporated by reference herein in its entirety.

General Overview

The high speed drill disclosed herein may include several mechanical components to enhance power transmission, minimize overheating, and to increase serviceable lifetimes. More specifically, the high speed drill may include a pair of ball connectors and an associated notch in the cutting tool configured to limit longitudinal motion of the cutting tool.

The high speed drill disclosed herein may further include a direct connection between the cutting burr and the motor shaft for the straight cutting burr. The high speed drill disclosed herein may further include a universal joint for transmitting rotary motion from the motor to the distal cutting tip for the angled cutting burr. The high speed drill disclosed herein may further include a clutch comprising a male cone connector and motor shaft connection including a threaded locking cylinder for the angled cutting burr.

Ball Connectors and Associated Notch

A first housing is configured for attachment of a straight cutting burr and a second housing is configured for attachment of an angled cutting burr. Each of the first housing and the second housing may comprise a pair of ball connectors. The pair of ball connectors may be configured for minimizing or eliminating longitudinal movement of the shaft of the straight cutting burr and the angled cutting burr within the housing assembly. The pair of ball connectors may be configured to reduce or eliminate axial movement of the cutting burr. A given burr shank may have a notch cut at a point along the length of the burr shank. The notch may be a groove cut around the circumference of the burr shank. The notch may form a semi-circular groove at a given point about the circumference of the burr shank. The notch may be configured to mate with a ball shaped connector. The burr may include one or more notches at specific points about the circumference of a burr shank. The burr may include a pair of opposed notches positioned radially opposite each other about the circumference of a burr shank.

The position of the pair of ball connectors and/or the position of the notch or notches determine the axial location of the distal end of the cutting burr distal tip. For the straight cutting burr, the position of the pair of ball connectors and/or the position of the notch may control engagement of the proximal end of the cutting burr with the motor shaft. For the angled cutting burr, the position of the pair of ball connectors and/or the position of the notch may control engagement of the cutting burr with a universal joint. Each of the pair of ball connectors may be positioned opposite each other radially about the shaft of the cutting burr.

Connection of Straight Cutting Burr with Motor Shaft

A straight cutting burr shank may be configured at a proximal end with an extension. The extension may be configured to mate with a notch in a motor shaft. A flat surface may be provided along the extension such that when the motor shaft turns, a corresponding flat surface of the motor shaft engages the flat surface on the extension and rotates the cutting burr tip, thereby grinding, shaving, or cutting desired tissue, bone, or bodily material. The flat surface on the extension and the corresponding mating surface on the motor shaft can transfer torque from the motor to the burr shank. The extension at a proximal end of the cutting burr shank may engage with a metal on metal fit, or a friction fit, and may transfer torque using surface contact. The flat surface may be configured as an edge of a polygonal shape on the extension, such as, for example, a triangular shape, a rectangular shape, a hexagonal shape, a wedge shape, a cone shape, or, alternatively, may be an engagement surface including grooves with corresponding notches, for example. The flat surface or engagement surface may be any surface capable of transferring torque from the motor to the cutting tip without slippage at the shaft/shank interface. Thus, the motor shaft is in direct connection with the burr shaft.

Figure 11:
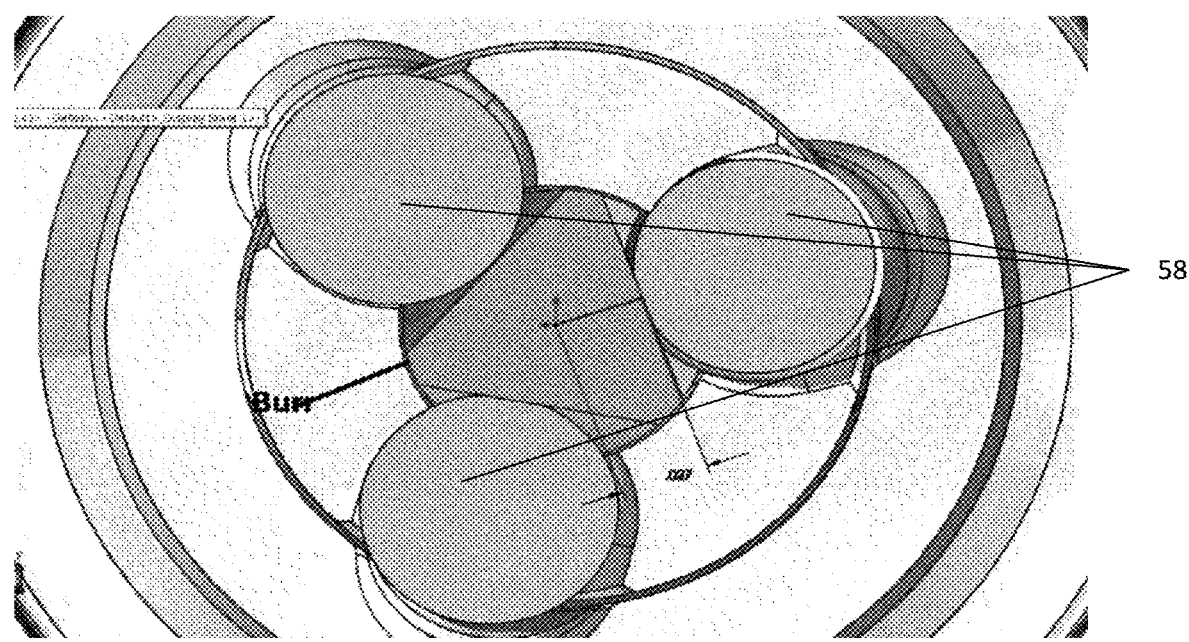
FIG. 11 illustrates a cross-sectional view bisecting the length of a burr.

Directly connecting the motor shaft to the burr shaft provides an advantage over conventional techniques which may employ a two-stage power train. In a two-stage power train, power is transmitted from a motor shaft to a drive shaft in a first stage and from the drive shaft to a burr shaft in a second stage. A two-stage power train may encourage chattering due to added structural components and the possibility of vibration between components. One example of a two-stage power train is shown in FIG. 11, which shows a 3 ball locking mechanism engaging an outer drive shaft to an inner burr shaft. This two-stage assembly is an example of an indirect connection with the motor shaft, as in this example the motor is connected to the drive shaft but not the burr shaft directly. Mechanisms such as those shown in FIG. 11 attempt to control both axial movement and transfer torque using a single connection.

The present teachings instead are directed toward direct connection of the cutting burr with the motor shaft for the straight cutting burr. The present teachings are directed toward separate mechanisms for limiting axial movement and transferring torque. Direct connection of the cutting burr with the motor shaft provides several advantages over conventional arrangements. More specifically, direct connection of the cutting burr with the motor shaft allows for improved power transmission efficiency, minimized heat losses, minimized part count, and offers the potential for longer serviceable lifetimes of the device. The direct connection of the cutting burr shank to the motor shaft is defined herein as a one-stage power train assembly.

Connection of Angled Cutting Burr with Motor Shaft

Due to the angled nature of the housing surrounding an angled cutting burr, a different mechanical configuration is required. An angled cutting burr may be defined herein as a cutting burr shank that is positioned at a different angle than a motor shaft. An angled cutting burr shank may attach to a universal joint located at a bend or break in an outer housing. A universal joint, or U-joint, may be positioned within a bent portion of the housing to transfer rotary motion to a distal tip. The universal joint may be connected on the opposite side to a drive shaft which engages with a motor shaft. A universal joint may be positioned between the burr shank of the angled cutting burr and the drive shaft. A universal joint may serve to connect a drive shaft with a burr shank. A universal joint may transmit rotary motion from a motor through a drive shaft to a cutting burr tip. A universal joint may allow for positioning the cutting tool through the space of a cone having an angle of greater than 20°, greater than 30°, greater than 40° or greater than 50° in relation to the axis of the motor. Greater angles may result in more stress on the joint. In specific embodiments, a universal joint may include a pair of hinges located close together, oriented at 90° with respect to each other, connected by a cross shaft.

Use of a universal joint may provide certain advantages over conventional devices, which may include a gear-to-gear power train positioned between the burr shank and the drive shaft of the angled cutting burr. More specifically, use of a universal joint may minimize heat generation and rapid vibrations and/or loud clicking noises (i.e. chattering).

An angled cutting burr shank may be configured at a proximal end with an extension. The extension may be configured to mate with a notch within a connector at the universal joint. A flat surface may be provided along the extension such that when the universal joint is turned, a corresponding flat surface of the universal joint engages the flat surface on the extension and rotates the cutting burr tip, thereby grinding, shaving, or cutting desired tissue, bone, or bodily material. The flat surface on the extension and the corresponding mating surface in the universal joint are configured to transfer torque. The extension at a proximal end of the cutting burr shank may engage with a metal on metal fit, or a friction fit, and may transfer torque using surface contact. The flat surface may be one or more surfaces of a polygonal shaped cross section on the extension, such as, for example, a triangular shape, a rectangular shape, a hexagonal shape, a wedge shape, a cone shape, or, alternatively, may be an engagement surface including grooves with corresponding notches, for example. The flat surface or engagement surface may be any surface capable of transferring torque from the universal joint to the cutting tip.

Clutch

In some embodiments, a clutch is provided for switching between operation using an angled cutting burr and a straight cutting burr. The clutch may include a clutch ring for locking a proximal end of a drive shaft joined axially with a motor shaft. The clutch may include one or more bearings that may engage with a motor directly for engaging or disengaging operation of one or more motor shafts. In some embodiments, a clutch may be provided on one section of a main body for connecting a cutting burr. In other embodiments, a clutch may be provided at an attachment point to a motor shaft for two or more sections of housing for attaching two or more cutting burrs.

The clutch may be configured as user-friendly interface. The clutch interface may be configured for enabling or disabling operation of a cutting burr. The clutch may be configured for enabling or disabling operation of an angled cutting burr. The clutch may be configured for enabling or disabling operation of a straight cutting burr. The clutch may be configured for engaging or releasing a set of bearings from a motor. The clutch may be configured for providing engagement or disengagement between a motor shaft and a drive shaft or a burr shank.

A clutch may include a threaded locking cylinder configured to slide along an axial direction, an engagement surface on a drive shaft or a burr shank, a spring, and an engagement surface formed as a cutout in an attachment portion of a motor shaft. During operation, a user may rotate the threaded locking cylinder about the longitudinal axis. A set of teeth extending from the threaded locking cylinder may engage with a set of threads positioned on an outer surface of the housing. A set of teeth may extend from the housing to facilitate movement along an axial direction as the threaded locking cylinder is rotated. As the threaded locking cylinder is rotated and slides toward a proximal end, a spring is compressed and an engagement surface on a drive shaft or a burr shank mates with a corresponding engagement surface on a motor shaft. As the clutch is engaged, a set of bearings may engage with a motor. A clutch ring locks all the components of the clutch in place prior to rotating the angled cutting burr or the straight cutting burr. The clutch ring may be mechanically linked to the threaded locking cylinder such that it is driven into a locked position by turning the threaded locking cylinder toward a proximal end of the drive shaft and disengaged by turning the threaded locking cylinder toward a distal end.

Engagement of the clutch may enable operation of the angled cutting burr. Disengagement of the clutch with the angled cutting burr tip attached or detached restricts use of the angled cutting burr. Thus, an end user may prefer to keep a straight cutting burr and an angled cutting burr attached to main body and engage the clutch only when operation of the angled cutting burr is desired. Engagement of the clutch at the second section necessarily disables operation of straight cutting burr.

Turning now to the drawings to illustrate example embodiments of the present teachings, FIG. 1 details one embodiment of the disclosure wherein a straight cutting burr 22 is positioned in the same plane as and 180° offset from an angled cutting burr 24 on a high speed drill 20. Main tubular member 28 houses connections for power, irrigation, and/or suction and connects to main body 26. Off of main body 26 extend two opposed sidearm extensions, first section 30 and second section 34. First section 30 houses straight cutting burr 22 and extends to first distal end 31 Second section 34 houses angled cutting burr 24 and extends to an opposed second distal end 35. An end-user may choose to have straight cutting burr 22, angled cutting burr 24, or both, connected at a given moment or for a given procedure.

Figure 2:
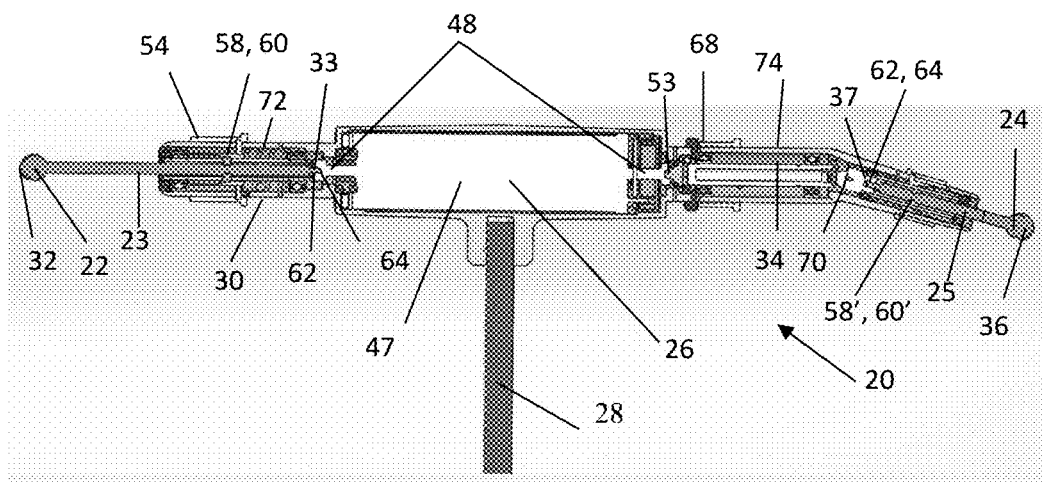
FIG. 2 illustrates a cross-sectional view of a high speed drill, in accordance with an embodiment of the disclosure.
Figure 3:
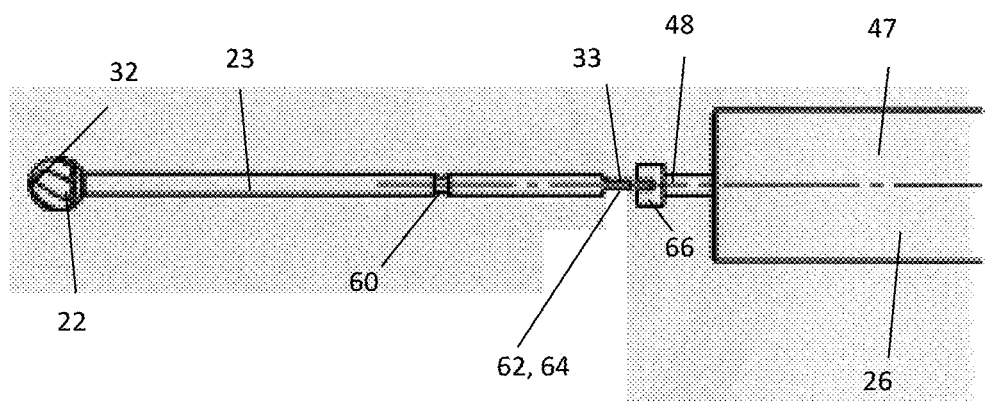
FIG. 3 illustrates a side view of a straight cutting burr tip and attachment into a housing, in accordance with an embodiment of the disclosure.
Figure 4:
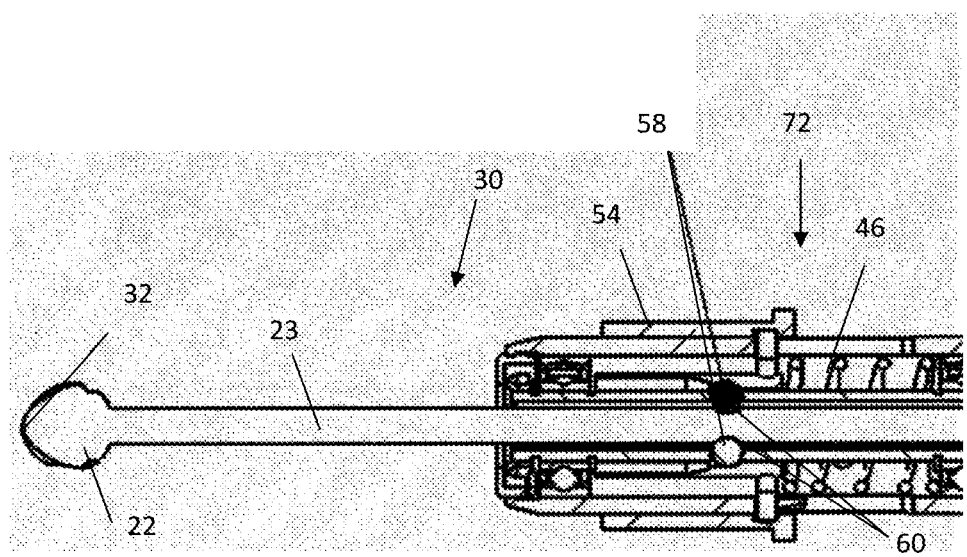
FIG. 4 illustrates a cross-sectional view of a straight cutting burr tip attached within a housing, in accordance with an embodiment of the disclosure.
Figure 6:
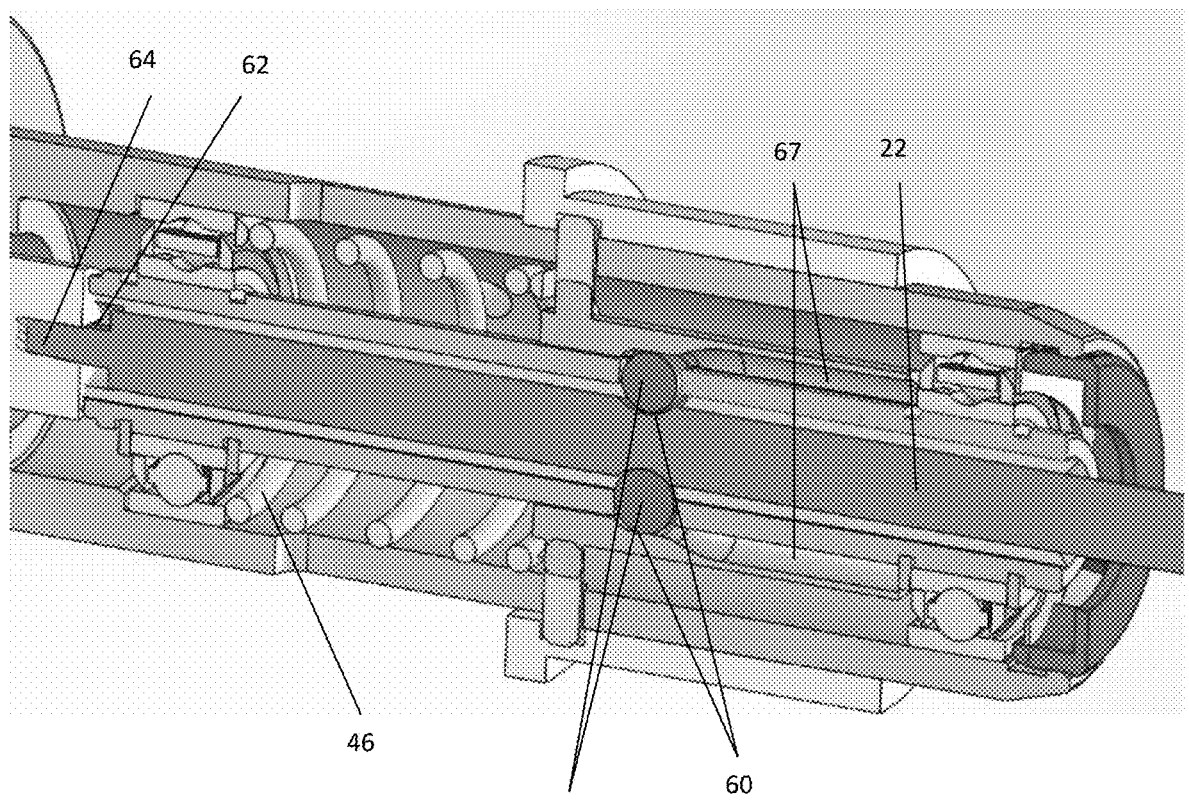
FIG. 6 illustrates a perspective cross-sectional view of a straight cutting burr within a housing, in accordance with an embodiment of the disclosure.

FIG. 2 illustrates a cross-section of FIG. 1 and highlights the mechanical interconnection between components in various aspects of high speed drill 20. In one aspect, a pair of ball connectors 58 are contained in a first housing 72 containing straight cutting burr 22. The ball connectors 58 may be biased inwardly by, for example, one or more springs. As shown in more detail in FIGS. 3-4, burr shank 23 has notch 60 cut at a point along the length of burr shank 23. As shown in FIG. 4, notch 60 is mated with a pair of ball connectors 58 within housing 72. FIG. 4 illustrates a cross-sectional view of straight cutting burr 22 and burr shank 23 contained in first housing 72 of first section 30. Two ball connectors 58 within first housing 72 engage with notch 60 at two radially opposed positions of burr shank 23 and are configured to axially retain the position of burr shank 23. Note that additional ball connectors may be used to engage notch 60. Similarly, for angled cutting burr 24, axial motion of burr shank 25 is illustrated as being limited by a pair of ball connectors 58' and notch 60', as shown in FIG. 2. The pair of ball connectors 58 is mechanically connected to housing 72 and are configured to limit longitudinal motion of straight cutting burr 22 after it has been locked in place within housing 72. Housing 72 further includes a spring 46, shown in FIGS. 4 and 6. Spring 46 provides a compressive force urging ball connectors 58 toward burr shank 23. Prior to insertion of burr shank 23 into housing 72, lock ring 54 is released, thereby releasing the spring forces from spring 46. As a result, ball connectors 58 are able to slide into cutouts 67, shown in FIG. 6, to allow space for burr shank 23 to slide easily into position. Following insertion of burr shank 23 into housing 72, lock ring 54 is re-positioned on housing 72, thereby compressing ball connectors 58 onto notch 60 and limiting axial movement of burr shank 23. When lock ring being is positioned in a locked position, the pair of ball connectors 58 are configured to be engaged within notch 60 and configured to limit axial movement of burr shank 23 within first section 30, as further illustrated in FIGS. 4 and 6.

Figure 5:
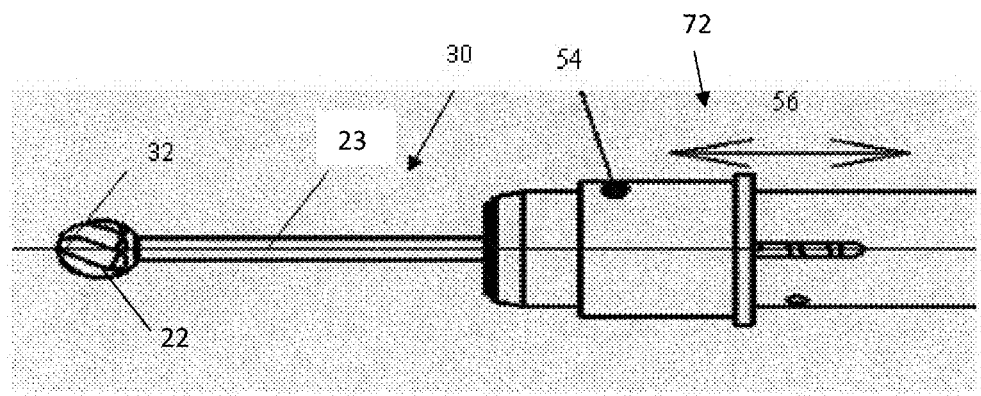
FIG. 5 illustrates a side view of a straight cutting burr tip contained within a housing, in accordance with an embodiment of the disclosure.
Figure 7:
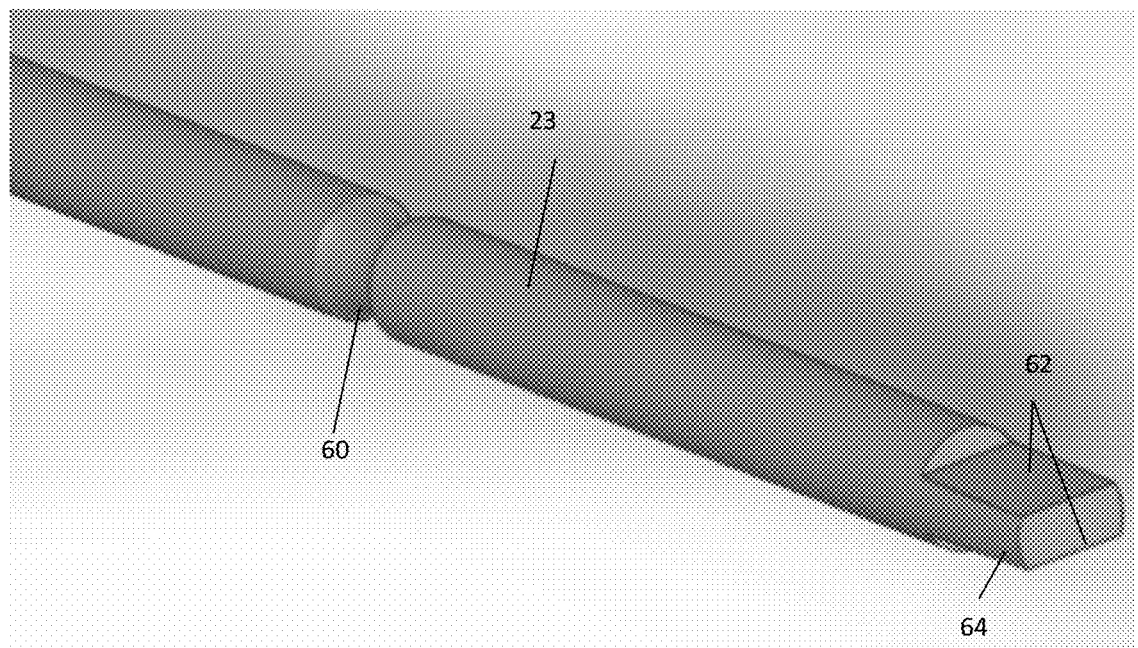
FIG. 7 illustrates a perspective view of a proximal end of a straight cutting burr, in accordance with an embodiment of the disclosure.

FIG. 5 illustrates a side view of first section 30, including straight cutting burr 22, burr shank 23, and housing 72. Housing 72 includes lock ring 54 which is positioned to lock burr shank 23 in position before operation of high speed drill 20, as described above. Lock ring 54 may be locked in place via a set screw using an allen key or the like to tighten it in position prior to operation of high speed drill 20. FIG. 7 highlights the proximal end of burr shank 23, including notch 60 and flat portions 62 on extension 64.

Referring to another aspect of the disclosure, shown in FIG. 2 are a pair of motor shafts 48 extending from motor 47. Motor 47 is contained in main body 26 of high speed drill 20. When high speed drill 20 is in cutting mode, power is sent through motor 47 and turns motor shaft 48 at speeds up to and including about 85,000 rpm. Transfer of torque is accomplished via extension 64 at proximal end 33 of burr shank 23, shown in FIGS. 2 and 3 for straight cutting burr 22. Extension 64 may be provided with one or more flat surfaces 62 to rotationally connect burr shank 23 and motor shaft 48. Extension 64 is configured to engage with square receiver 66 which is configured with a set of mating flat surfaces. Square receiver 66 is an extension of motor shaft 48 configured for metal to metal engagement with proximal end 33 of burr shank 23. Motor shaft 48, in turn, causes high speed rotational motion at distal tip 32 of straight cutting burr 22 or distal tip 36 of angled cutting burr 24.

Figure 9:
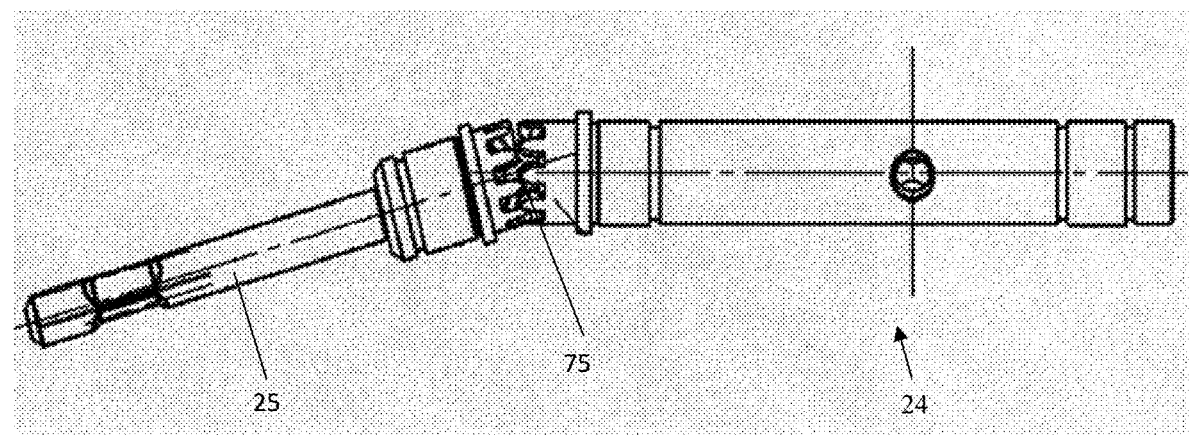
FIG. 9 illustrates a side view of an angled cutting burr contained within a housing.

Similarly, transfer of torque is accomplished via extension 64 at proximal end 37 of burr shank 25, shown in FIG. 2 for angled cutting burr 24. However, transfer of torque for angled cutting burr 24 also involves transferring rotary motion from motor shaft 47 through a joint to burr shank 25. One conventional method for transferring rotary motion to an angled burr tip is shown in FIG. 9. Gear-to-gear power train 75 is configured to connect a drive shaft to a burr shaft. Other conventional methods for transferring rotary motion to an angled burr tip include use of a bevel gear. Use of a gear-to-gear power train or a bevel gear may generate substantial heat and noise. Friction may be created between the gears, particularly during high speed operation, and noise may be created by the mechanical impact of the gear teeth. Temperatures at the gear-to-gear power train or bevel gear may reach upwards of 70-80° C. during operation in continuous mode for 3-5 minutes without load. Additionally, a gear-to-gear power train or bevel gear may be likely to experience rapid vibrations and/or chattering.

Figure 8:
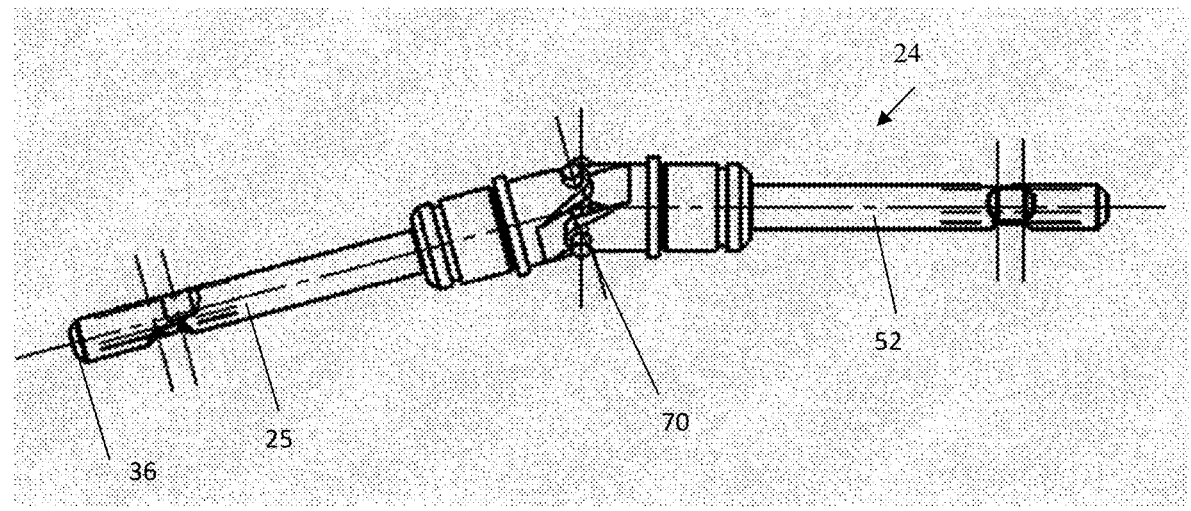
FIG. 8 illustrates a side view of an angled cutting burr, in accordance with an embodiment of the disclosure.

In contrast to the gear-to-gear power train, one aspect of the present disclosure related to angled cutting burr 24 is highlighted in FIG. 8. Universal joint 70 provides several advantages over conventional methods. Universal joint 70 provides a mechanism for transferring rotary motion from drive shaft 52 to burr shank 25, designed for reducing noise and heat generation. Use of universal joint 70 is configured to result in less friction, reduced impact and reduced thrust force on the bearing. Use of universal joint 70 is configured to result in longer serviceable lifetimes of high speed drill 20.

Figure 10A:
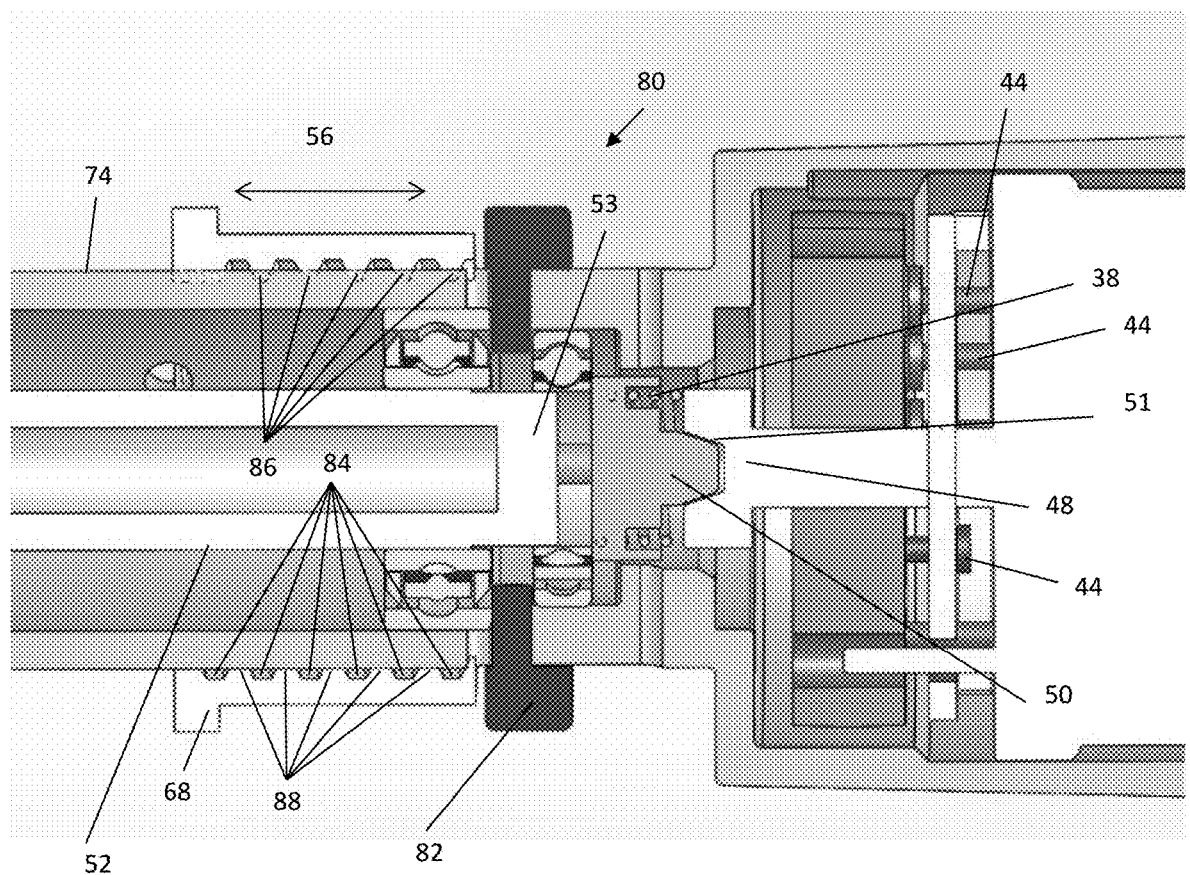
FIG. 10A illustrates a cross-sectional view of a proximal end of an angled cutting burr and connections into a main body, in accordance with an embodiment of the disclosure.
Figure 10B:
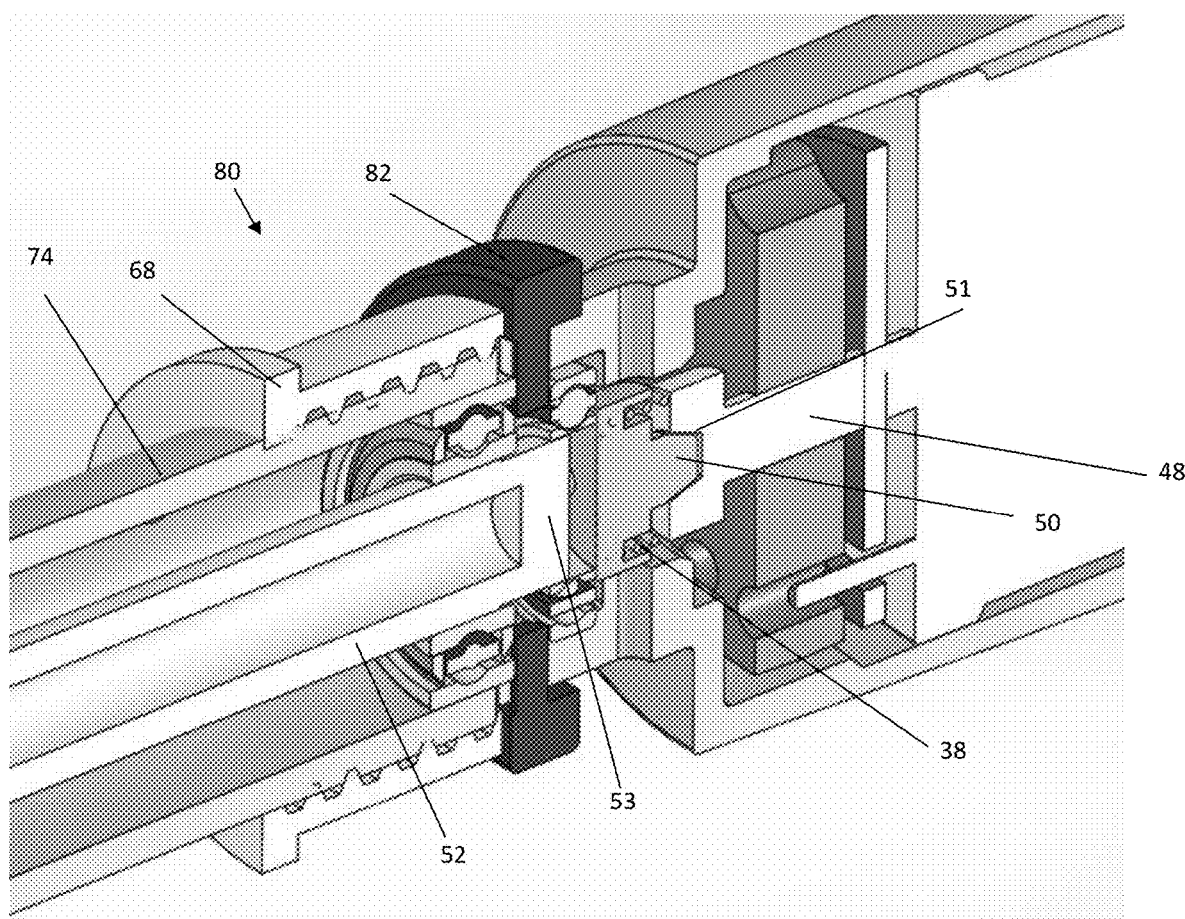
FIG. 10B illustrates a cross-sectional perspective view of a proximal end of an angled cutting burr and connections into a main body, in accordance with an embodiment of the disclosure.

In one aspect of the present disclosure, a clutch is included, for example, as shown in FIGS. 2 and 10A-B. Clutch 80 is configured to provide user-friendly control to an end user in switching between an angled cutting burr 24 and a straight cutting burr 22. In the illustrated embodiment, clutch 80 includes clutch ring 82 which is configured for locking and unlocking clutch 80, threaded locking cylinder 86 which is configured to slide along axial direction 56, male cone 50, spring 38, and female cone 51 formed as a cutout in square receiver 66 extending from motor shaft 48.

During operation, a user may rotate threaded locking cylinder about the longitudinal axis. A set of threads 88 extending from threaded locking cylinder 68 engage with a set of corresponding threads 84 positioned on an outer surface of housing 74. A set of corresponding threads 84 extending from housing 74 facilitate movement along axial direction 56 as threaded locking cylinder 68 is rotated. Threaded groove 86 engages an inner portion of each of threads 88 within housing 74. As threaded locking cylinder 68 is rotated and slides toward proximal end 53, spring 38 is compressed and male cone 50 engages with female cone 51 in motor shaft 48. As clutch 80 is engaged, a set of bearings 44 engage with motor 47. Clutch ring 82 locks all the components of clutch 80 in place prior to operation of angled cutting burr 24. Clutch ring 82 is mechanically linked to threaded locking cylinder 68 such that it is driven into a locked position by turning threaded locking cylinder 68 toward proximal end 53 of drive shaft 52 and disengaged by turning threaded locking cylinder 68 toward a distal end.

Engagement of clutch 80 enables operation of angled cutting burr 24. Disengagement of clutch 80 with angled cutting burr tip attached or detached, restricts use of angled cutting burr 24. Thus, an end user may prefer to keep a straight cutting burr 22 and an angled cutting burr 24 attached to main body 26 and engage clutch 80 only when operation of angled cutting burr 24 is desired. Engagement of clutch 80 at the second section 34 necessarily disables operation of straight cutting burr 22.

If an end user plans a first operation stage using a straight cutting burr 22 and a second operation stage using an angled cutting burr 24, the following steps may be performed: 1. Insert straight cutting burr 22 and perform grinding, shaving, or cutting desired tissue, bone, and/or other bodily material; 2. Remove straight cutting burr 22; 3. Flip the hand piece 180°; 4. Insert angled cutting burr 24; 5. Activate clutch ring; 6. Perform grinding, shaving, or cutting desired tissue, bone, and/or other bodily material using angled cutting burr 24.

If an end user plans a first operation stage using an angled cutting burr 24 and a second operation stage using a straight cutting burr 22, the following steps may be performed: 1. Insert angled cutting burr 24; 2. Activate clutch ring; 3. Perform grinding, shaving, or cutting desired tissue, bone, and/or other bodily material using angled cutting burr 24; 4. Release clutch ring; 5. Remove angled cutting burr 24; 6. Flip the hand piece 180°; 7. Insert straight cutting burr 22; 5.; 8. Perform grinding, shaving, or cutting desired tissue, bone, and/or other bodily material using straight cutting burr 22.

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

ELEMENT NUMBERS 20 high speed drill
22 straight cutting burr
23 burr shank (straight)
24 angled cutting burr
25 burr shank (angled)
26 main body
28 main tubular member
30 first section (straight)
31 distal end
32 first distal end
33 proximal end (first, straight)
34 second section (angled)
35 distal end
36 second distal end
37 second proximal end (burr shank)
38 spring (small)
40 motor
42 power source
44 bearing
46 spring
47 motor
48 motor shaft
50 male cone
51 female cone
52 drive shaft
53 proximal end (drive shaft)
54 lock ring
56 direction (longitudinal motion)
58 ball connector
58' ball connector
60 notch
60' notch
62 flat surface
64 extension
66 square receiver
67 cutout
68 threaded locking cylinder
69 teeth
70 universal joint
72 first housing (straight)
74 second housing (angled)
75 gear to gear power train
80 clutch
82 clutch ring
84 corresponding threads (extending from housing)
86 threaded groove
88 threads (extending from threaded locking cylinder)

What is claimed is:

1. A medical device, comprising:
a main body having a first section at a first end of the main body and a second section at an opposite second end of the main body, the first section comprising a first housing configured to be operably connectable to a first cutting tip, and the second section comprising a second housing configured to be operably connectable to a second cutting tip; and
an electrical motor disposed inside the main body, the electrical motor configured to be in electrical communication with a power source.

2. The medical device of claim 1, wherein the first section and the second section are positioned 180° opposed from each other on the main body.

3. The medical device of claim 1, wherein the first cutting tip is a straight cutting burr and the second cutting tip is an angled cutting burr, wherein the first cutting tip and the second cutting tip are not mechanically connected to the electrical motor at a given time.

4. The medical device of claim 1, wherein the electrical motor is configured to transfer power to the first cutting tip or the second cutting tip via a one-stage power train assembly.

5. The medical device of claim 1, wherein a motor shaft is configured to transfer torque from the electrical motor to a burr shank through an extension from the burr shank engaged with the motor shaft.

6. The medical device of claim 1, wherein a motor shaft is configured to transfer torque from the electrical motor to a burr shank through an extension from a drive shaft engaged with the motor shaft.

7. The medical device of claim 1, further comprising a pair of ball connectors resiliently contained within at least the first housing.

8. The medical device of claim 7, wherein the pair of ball connectors are positioned opposite each other radially about a shaft of the first cutting tip or the second cutting tip.

9. The medical device of claim 8, wherein the pair of ball connectors are configured to limit axial motion of the first cutting tip or the second cutting tip and configured to rotate during rotation of a burr shank.

10. The medical device of claim 1, wherein the second housing comprises a universal joint.

11. The medical device of claim 10, wherein the second housing further comprises a male cone configured to engage with a motor shaft.

12. The medical device of claim 1, further comprising a clutch for limiting operation to a single one of the cutting tips at a time.

13. The medical device of claim 12, wherein the clutch includes a clutch ring.

14. The medical device of claim 13, wherein the clutch ring is configured to engage a set of bearings adjacent the electrical motor to permit rotational motion of a motor shaft extend from the electric motor.

15. A medical instrument comprising:
a hand piece having a first end and a second end, the first end configured to be detachably connectable to a first cutting tip, and the second end configured to be detachably connectable to a second cutting tip; and
an electrical motor disposed inside the hand piece, the electrical motor configured to be in electrical communication with a power source,
wherein the first cutting tip and the second cutting tip are not both mechanically connected to the electrical motor at a given time.

16. The medical instrument of claim 15, wherein the electrical motor is configured to transfer torque via a first mechanism and a housing is configured to limit axial motion of a burr shank via a second mechanism.

17. A medical device comprising:
a main body;

an electrical motor on the main body, where the electrical motor is configured to be in electrical communication with a power source;

a first cutting tip attached to a first section of the main body; and a second cutting tip attached to a second section of the main body;

where the first cutting tip and the second cutting tip are both configured to be moved by the electrical motor, where connections of the first cutting tip and the second cutting tip to the electrical motor are configured to limit a transfer of power from the electrical motor in an alternative fashion to either:

a transfer of power from the electrical motor to the first cutting tip, or a transfer of power from the electrical motor to the second cutting tip; and where the first section is at a first end of the main body and the second section is at an opposite second end of the main body.

18. The medical device of claim 17 where the connections comprise a clutch for limiting operation of the cutting tips to a single one of the cutting tips at a time.

19. The medical device of claim 17 where at least one of the connections comprises one or more of:
a plurality of ball connectors,
a universal joint,
interlockable male and female cones, or
a clutch.

\* \* \* \* \*